(12) United States Patent
Hara

(10) Patent No.: US 11,464,403 B2
(45) Date of Patent: Oct. 11, 2022

(54) TRACHEAL TUBE INSERTION AID KIT

(71) Applicant: TEIKYO UNIVERSITY, Tokyo (JP)

(72) Inventor: Yoshiki Hara, Tokyo (JP)

(73) Assignee: TEIKYO UNIVERSITY, Tokyo (JP)

( * ) Notice: Subject to any disclaimer, the term of this patent is extended or adjusted under 35 U.S.C. 154(b) by 372 days.

(21) Appl. No.: 16/479,492

(22) PCT Filed: Nov. 22, 2017

(86) PCT No.: PCT/JP2017/042099
§ 371 (c)(1),
(2) Date: Jul. 19, 2019

(87) PCT Pub. No.: WO2018/135131
PCT Pub. Date: Jul. 26, 2018

(65) Prior Publication Data
US 2019/0380569 A1    Dec. 19, 2019

(30) Foreign Application Priority Data

Jan. 23, 2017  (JP) .............................. JP2017-009377
Apr. 14, 2017  (JP) .............................. JP2017-080684

(51) Int. Cl.
*A61B 1/267*   (2006.01)
*A61M 16/04*   (2006.01)

(52) U.S. Cl.
CPC ............. *A61B 1/267* (2013.01); *A61M 16/04* (2013.01)

(58) Field of Classification Search
CPC ...... A61B 1/267; A61B 1/2673; A61B 1/2676
See application file for complete search history.

(56) References Cited

U.S. PATENT DOCUMENTS 4,211,234 A  * 7/1980  Fisher .............. A61M 16/0488
                                                                 128/200.26
4,557,256 A  * 12/1985 Bauman ................. A61B 1/267
                                                                      600/193

(Continued)

FOREIGN PATENT DOCUMENTS

CN        2812972 Y      9/2006
CN       201082289 Y     7/2008

(Continued)

OTHER PUBLICATIONS

Office Action dated May 27, 2021 in corresponding Chinese Application No. 201780084090.9 and its English translation.

(Continued)

*Primary Examiner* — Jan Christopher L Merene
(74) *Attorney, Agent, or Firm* — Jon E. Gordon; Haug Partners LLP

(57) ABSTRACT

A tracheal tube insertion aid kit (1) assists in inserting a tracheal tube (9) from an oral cavity (B) of a patient (A) into an endotracheal space (E) through a glottis (D) using an indirect glottis viewing type laryngoscope (2) not equipped with the tracheal tube (9). The tracheal tube insertion aid kit (1) includes a guide tube (11) having flexibility and formed to be insertable into the endotracheal space (E) from the oral cavity (B) through the glottis (D), and a guide wire (12) formed to be insertable through the inside of the guide tube (11) and insertable into the endotracheal space (E) from the oral cavity (B) through the glottis (D).

8 Claims, 9 Drawing Sheets

(56) References Cited

U.S. PATENT DOCUMENTS

| | | | | |
|---|---|---|---|---|
| 4,982,729 A * | 1/1991 | Wu | ............ | A61B 1/07 |
| | | | | 128/200.26 |
| 5,323,771 A * | 6/1994 | Fisher | ............ | A61M 16/0488 |
| | | | | 128/200.26 |
| 6,146,402 A | 11/2000 | Munoz | | |
| 9,775,505 B2 * | 10/2017 | McGrath | ............ | A61B 1/267 |
| 2007/0093693 A1 * | 4/2007 | Geist | ............ | A61B 1/00066 |
| | | | | 600/199 |
| 2009/0065000 A1 * | 3/2009 | Chen | ............ | A61M 16/0418 |
| | | | | 128/200.26 |
| 2009/0318769 A1 * | 12/2009 | Tenger | ............ | A61B 5/0071 |
| | | | | 600/199 |
| 2011/0270038 A1 * | 11/2011 | Jiang | ............ | A61B 1/267 |
| | | | | 600/188 |
| 2014/0135583 A1 * | 5/2014 | Moreno | ............ | A61B 1/267 |
| | | | | 600/199 |
| 2014/0378770 A1 | 12/2014 | Dhonneur | | |

FOREIGN PATENT DOCUMENTS

| | | |
|---|---|---|
| CN | 201337437 Y | 11/2009 |
| CN | 101642365 A | 2/2010 |
| CN | 102448363 A | 5/2012 |
| CN | 202505930 U | 10/2012 |
| CN | 104147671 A | 11/2014 |
| CN | 104302345 A | 1/2015 |
| CN | 105407786 A | 3/2016 |
| JP | A-02-174858 | 7/1990 |
| JP | A-07-505304 | 6/1995 |
| JP | A-10-165504 | 6/1998 |
| JP | A-2002-000732 | 1/2002 |
| JP | A-2006-122181 | 5/2006 |
| JP | A-2010-012173 | 1/2010 |
| JP | A-2011-030863 | 2/2011 |
| WO | WO 2016/044438 A1 | 3/2016 |

OTHER PUBLICATIONS

Akihiro Suzuki, "DAM and indirect glottis-viewing laryngoscope", The Journal of Japan Society for Clinical Anesthesia, 2010, vol. 30, No. 4, p. 585-592 and its English translation.

International Search Report and Written Opinion dated Feb. 20, 2018 in corresponding International Application No. PCT/JP2017/042099 and the English translation of the International Search Report.

Office Action dated Jan. 13, 2022 in corresponding Chinese Application No. 201780084090.9 and its English translation.

Notice of Allowance dated May 31, 2022 in corresponding Chinese Patent Application No. 201780084090.9 and its English translation.

* cited by examiner

FIG. 4
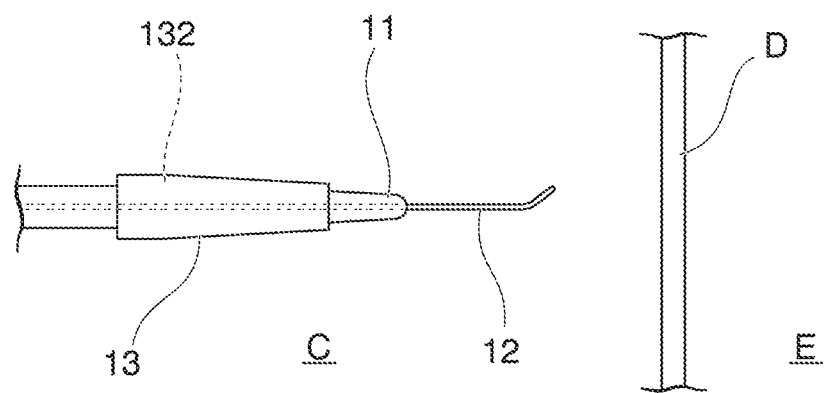
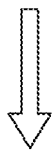
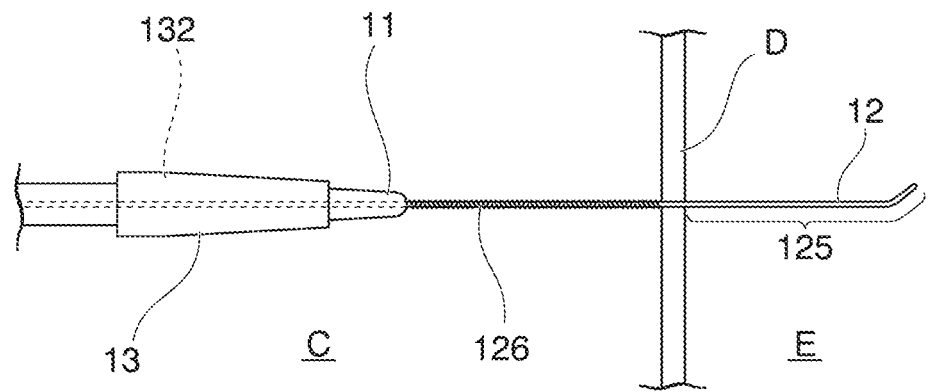

*FIG. 5*
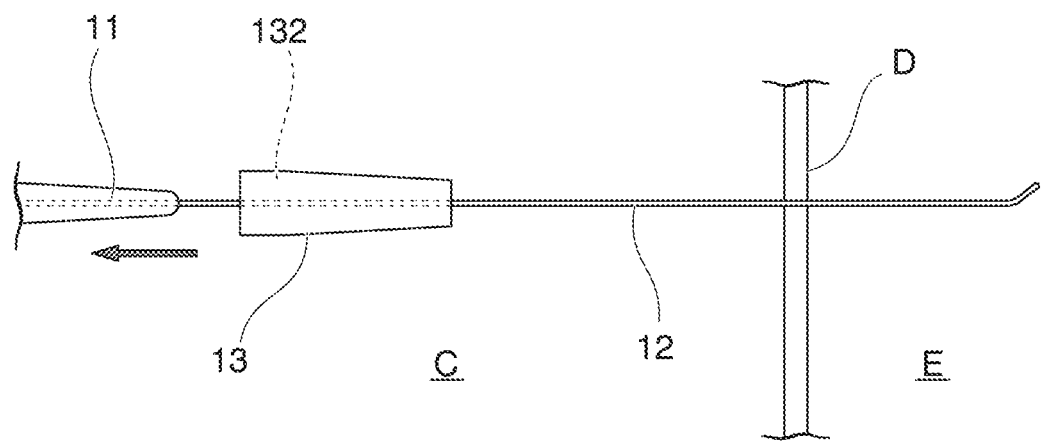
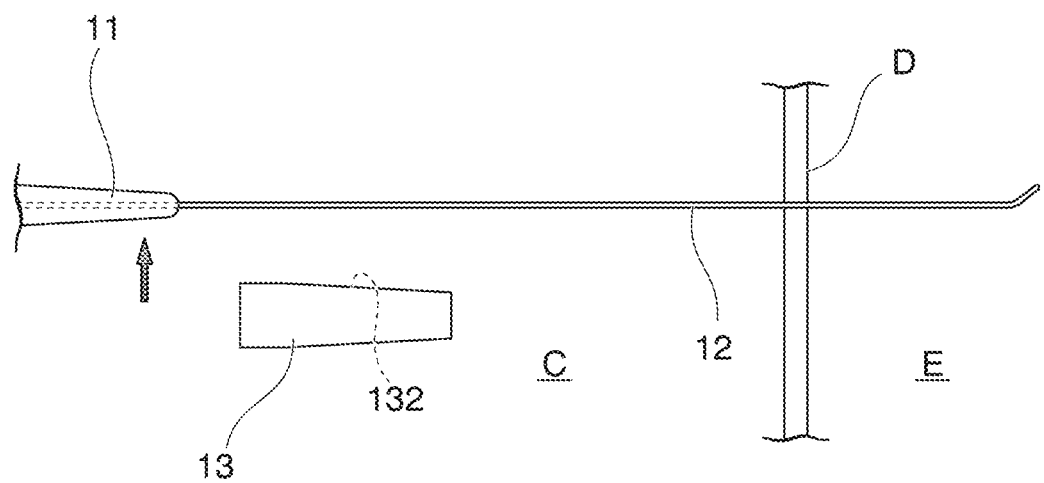

FIG. 6
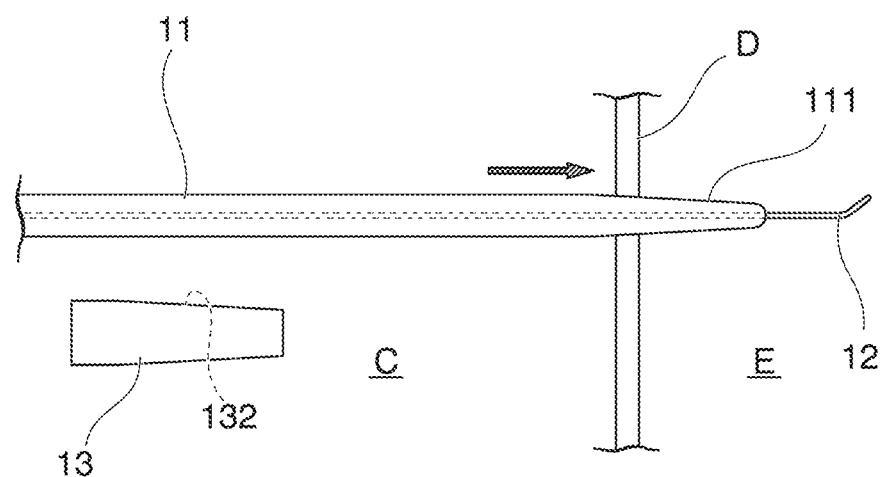
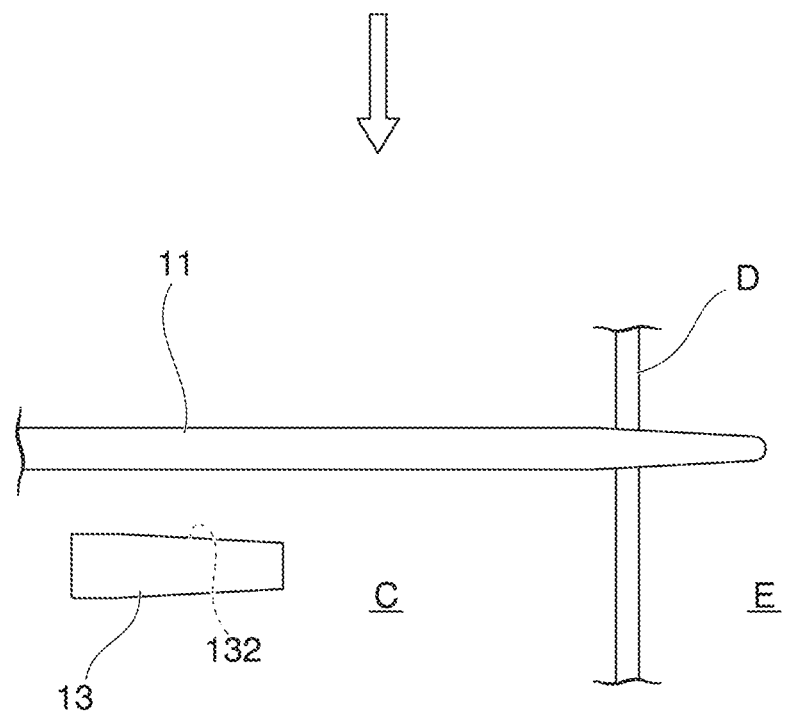

FIG. 7
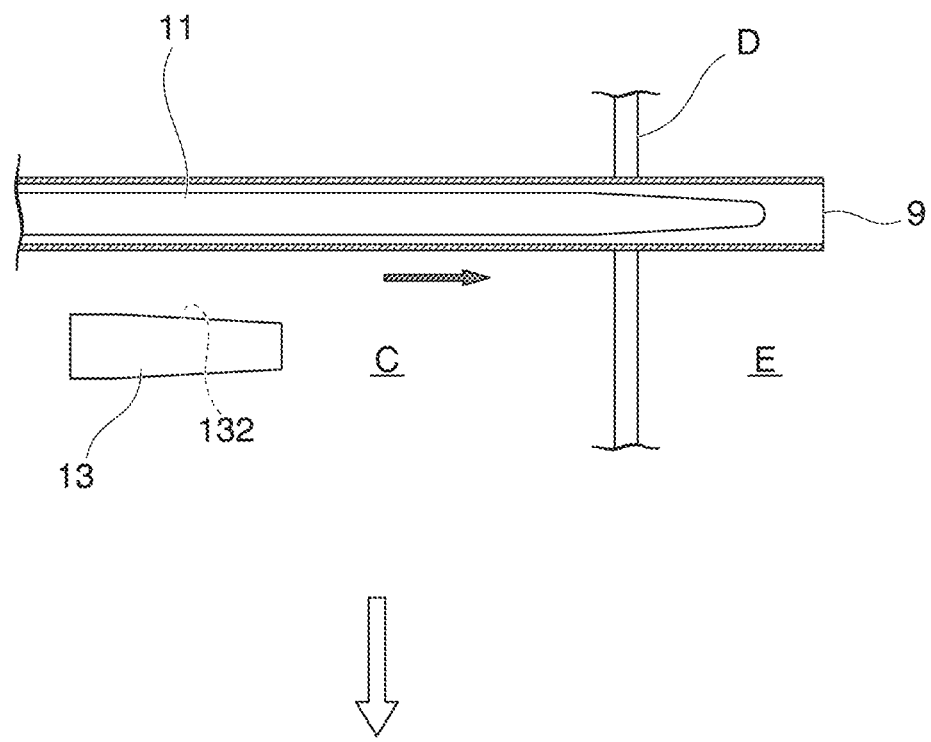
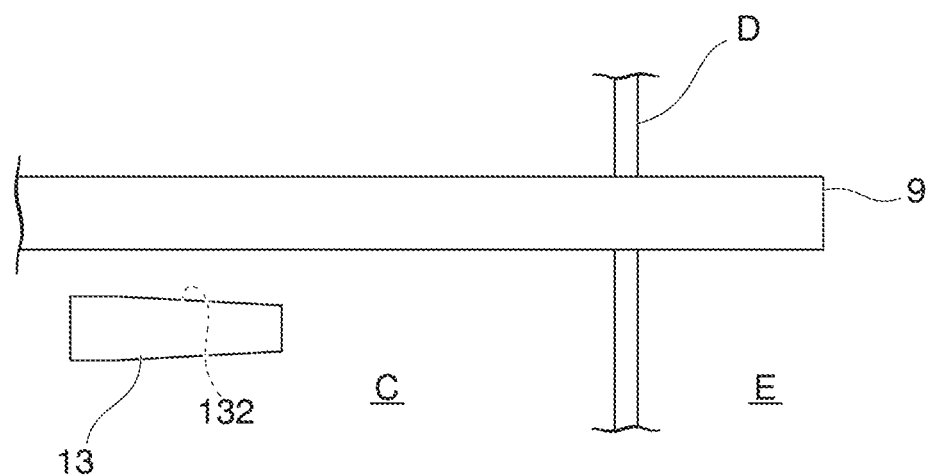

TRACHEAL TUBE INSERTION AID KIT

TECHNICAL FIELD

The present invention relates to a tracheal tube insertion aid kit which is the National Stage entry under 35 U.S.C. § 371 of International Application No. PCT/JP2017/042099 filed on Nov. 22, 2017, published on Jul. 26, 2018 under Publication Number WO 2018/135131 A1, which priority is claimed on Japanese Patent Application No. 2017-009377 filed on Jan. 23, 2017 and Japanese Patent Application No. 2017-080684 filed on Apr. 14, 2017, the contents of which are incorporated herein by reference, in their entirety.

BACKGROUND ART

Conventionally, when performing anesthesia on a patient, for example, a tracheal tube may be inserted into an endotracheal space from an oral cavity of the patient through a glottis, and then an anesthetic gas is fed from the tracheal tube into the endotracheal space.

As a laryngoscope for observing the larynx while viewing the glottis, there are indirect glottis viewing type laryngoscopes through which the glottis can be indirectly viewed (see, for example, Non-Patent Document 1). Indirect glottis viewing type laryngoscopes include a laryngoscope not equipped with a tracheal tube (hereinafter referred to as a "second-generation video-laryngoscope"). Since a second-generation video-laryngoscope enables the larynx to be observed or to be treated while being observed, second-generation video-laryngoscopes have wide applicability.

CITATION LIST

Non-Patent Document

[Non-Patent Document 1]
Suzuki Akihiro, "DAM and Indirect Glottis Viewing Laryngoscope," Japanese Journal of Clinical Anesthesiology, 2010, Vol. 30, No. 4, P585-592

SUMMARY OF INVENTION

Technical Problem

As described above, when a tracheal tube is inserted into an endotracheal space using a second-generation video-laryngoscope, the glottis can be indirectly viewed through an observing point positioned in an intraoral space of the second-generation video-laryngoscope.

Here, when the tracheal tube is inserted into the endotracheal space, a linear approach connecting the extraoral space and the glottis is necessary. However, a gap between a straight line connecting the glottis from the observing point positioned in the intraoral space of the second-generation video-laryngoscope and a path of the tracheal tube is large. For this reason, although the glottis can be indirectly viewed with a second-generation video-laryngoscope, it cannot be said that the tracheal tube can always be easily inserted into the glottis, and there is room for improvement in this respect.

An aspect of the present invention is directed to provide a tracheal tube insertion aid kit capable of easily inserting a tracheal tube into an endotracheal space.

Solution to Problem

A first aspect of the present invention is a tracheal tube insertion aid kit configured to assist in inserting a tracheal tube from an oral cavity of a patient into an endotracheal space through a glottis using an indirect glottis viewing type laryngoscope, the tracheal tube insertion aid kit including a guide tube formed to be insertable into the endotracheal space from the oral cavity through the glottis, and a guide wire formed to be insertable through the inside of the guide tube and insertable into the endotracheal space from the oral cavity through the glottis, in which at least a portion on a distal end side of the guide tube has flexibility.

In a second aspect of the present invention, the portion on the distal end side of the guide tube may be formed in a tapered shape.

In a third aspect of the present invention, a corner of the portion on the distal end side of the guide tube may be formed to be rounded.

In a fourth aspect of the present invention, a holding part detachably holding the guide tube in a state in which a distal end of the guide tube is disposed on a distal end side of the blade of the laryngoscope may be provided at a portion that is observable with the laryngoscope.

In a fifth aspect of the present invention, the holding part may be integrally formed on the blade.

A sixth aspect of the present invention may include an introducing member disposed to extend along the blade of the laryngoscope and configured to introduce the guide tube into the endotracheal space, in which the introduction member is deformable and able to be held in a predetermined shape, and the holding part is provided at a first end portion of the introducing member which is disposed on a distal end side of the blade.

In a seventh aspect of the present invention, a grab part formed in a deformable plate shape and configured to be gripped by a user together with a grip part of the blade may be provided at a second end portion of the introducing member.

In an eighth aspect of the present invention, the blade may include an insertion part formed to be curved in an arc shape and configured to be inserted into an intraoral space of the patient, in which a cross-sectional shape perpendicular to a direction in which the introducing member extends is formed in a U shape having an opening on an inner side in the radial direction of the insertion part formed in an arc shape.

In a ninth aspect of the present invention, an engaging part engageable with the blade may be provided at the first end portion of the introducing member.

In a tenth aspect of the present invention, the holding part may be formed in a tubular shape and in a tapered shape toward the distal end side of the blade and may detachably hold the guide tube with the guide tube inserted therethrough, and a slit which allows the guide wire to be exposed to the outside while inserted through the inside of the holding part may be provided on a circumferential surface of the holding part.

Advantageous Effects of Invention

According to the first aspect of the present invention, the guide tube and the guide wire are provided. Thus, after the guide wire is inserted into the endotracheal space and arranged, the guide tube is guided by the guide wire to be inserted into the endotracheal space and arranged, and thereby the tracheal tube can be inserted along the guide tube into the endotracheal space. Since at least the portion on the distal end side of the guide tube has flexibility, a bent state of the portion on the distal end side of the guide tube can be adjusted according to a difference in position of the glottis or the like for each patient. Therefore, the tracheal tube insertion aid kit according to the first aspect can easily insert the tracheal tube into the endotracheal space.

According to the second aspect of the present invention, the portion on the distal end side of the guide tube is formed in a tapered shape. Thereby, it is possible to easily pass the guide tube through the glottis. Therefore, the tracheal tube insertion aid kit according to the second aspect can improve workability when the tracheal tube is inserted.

According to the third aspect of the present invention, the corner of the portion on the distal end side of the guide tube is formed to be rounded. Thereby, when the guide tube is inserted into the endotracheal space, damage can be limited even when the distal end of the guide tube hits a portion from the intraoral space to the endotracheal space. Therefore, the tracheal tube insertion aid kit according to the third aspect can prevent damage to a portion from the intraoral space to the endotracheal space in the operation for inserting the tracheal tube.

According to the fourth aspect of the present invention, the holding part detachably holding the guide tube is provided at a portion that is observable with the laryngoscope. According to this configuration, by inserting the blade into the intraoral space in a state in which the guide tube is held by the holding part, the guide tube is disposed with the distal end directed toward the glottis. Therefore, the guide tube can be easily arranged compared to a case in which the guide tube is inserted alone into the intraoral space, and damage to the intraoral space due to the distal end of the guide tube can be limited. Therefore, the tracheal tube insertion aid kit according to the fourth aspect can prevent damage in the intraoral space while improving the workability at the time of inserting the tracheal tube.

According to the fifth aspect of the present invention, the holding part is formed in a tubular shape and in a tapered shape to detachably hold the guide tube in a state in which the guide tube is inserted therethrough, and the slit is provided in the holding part. Thereby, the guide tube is pulled out of the holding part and easily removed. The guide wire can be easily removed from the holding part by operating the guide tube to move the guide wire outward in a radial direction of the holding part and pass through the slit. Therefore, the tracheal tube insertion aid kit according to the fifth aspect can further improve the workability when the tracheal tube is inserted.

According to the sixth aspect of the present invention, the introducing member that is deformable and can be held in a predetermined shape is provided, and the holding part is provided at the first end portion of the introducing member which is disposed on the distal end side of the blade. Thereby, the guide tube can be introduced after the introducing member is deformed according to a difference in position of the glottis or the like for each patient and the position of the holding part is adjusted. Since the holding part is provided at first end portion of the end portions of the introducing member which is disposed on the distal end side of the blade, the guide tube can be easily held by the holding part after being introduced.

Therefore, the tracheal tube insertion aid kit according to the sixth aspect can further improve the workability when the tracheal tube is inserted.

According to the seventh aspect of the present invention, the grab part configured to be gripped by a user together with the grip part of the blade is provided at the second end portion of the introducing member. Thereby, the user can insert the guide wire into the endotracheal space in a state in which the introducing member and the guide tube are reliably positioned. Therefore, the tracheal tube insertion aid kit according to the seventh aspect can further improve the workability when the tracheal tube is inserted.

According to the eighth aspect of the present invention, a cross-sectional shape perpendicular to a direction in which the introducing member extends is formed in a U shape having an opening on an inner side in the radial direction of the insertion part formed in an arc shape. Thus, the user can introduce the guide tube from the U-shaped opening side and introduce the guide tube while it is in contact with the inner wall of the introducing member. Therefore, the tracheal tube insertion aid kit according to the eighth aspect can further improve the workability at the time of inserting the tracheal tube.

According to the ninth aspect of the present invention, since the engaging part that is engageable with the blade is provided at the first end portion of the introducing member, the holding part can be reliably positioned by fixing the first end portion of the introducing member to the blade by the engaging part. Therefore, the tracheal tube insertion aid kit according to the ninth aspect can further improve the workability at the time of inserting the tracheal tube.

According to the tenth aspect of the present invention, since the holding part is integrally formed on the blade, the number of parts can be reduced compared to a case in which the holding part and the blade are separately formed. Therefore, the tracheal tube insertion aid kit according to the tenth aspect can achieve a cost reduction.

BRIEF DESCRIPTION OF DRAWINGS

FIG. 4 is a view of when a guide wire of the embodiment is inserted into an endotracheal space.

FIG. 5 is a view of when the guide tube and the guide wire of the embodiment are removed from a holding part.

FIG. 6 is a view of when the guide tube of the embodiment is inserted into the endotracheal space and a view of when the guide wire is pulled out of the guide tube.

FIG. 7 is a view of when the tracheal tube of the embodiment is inserted into the endotracheal space and a view of when the guide tube is exposed to the outside of the oral cavity.

DESCRIPTION OF EMBODIMENTS

Hereinafter, embodiments of the present invention will be described with reference to the drawings.

A tracheal tube insertion aid kit 1 according to one embodiment of the present invention will be described with reference to FIGS. 1 to 7.

Figure 1:
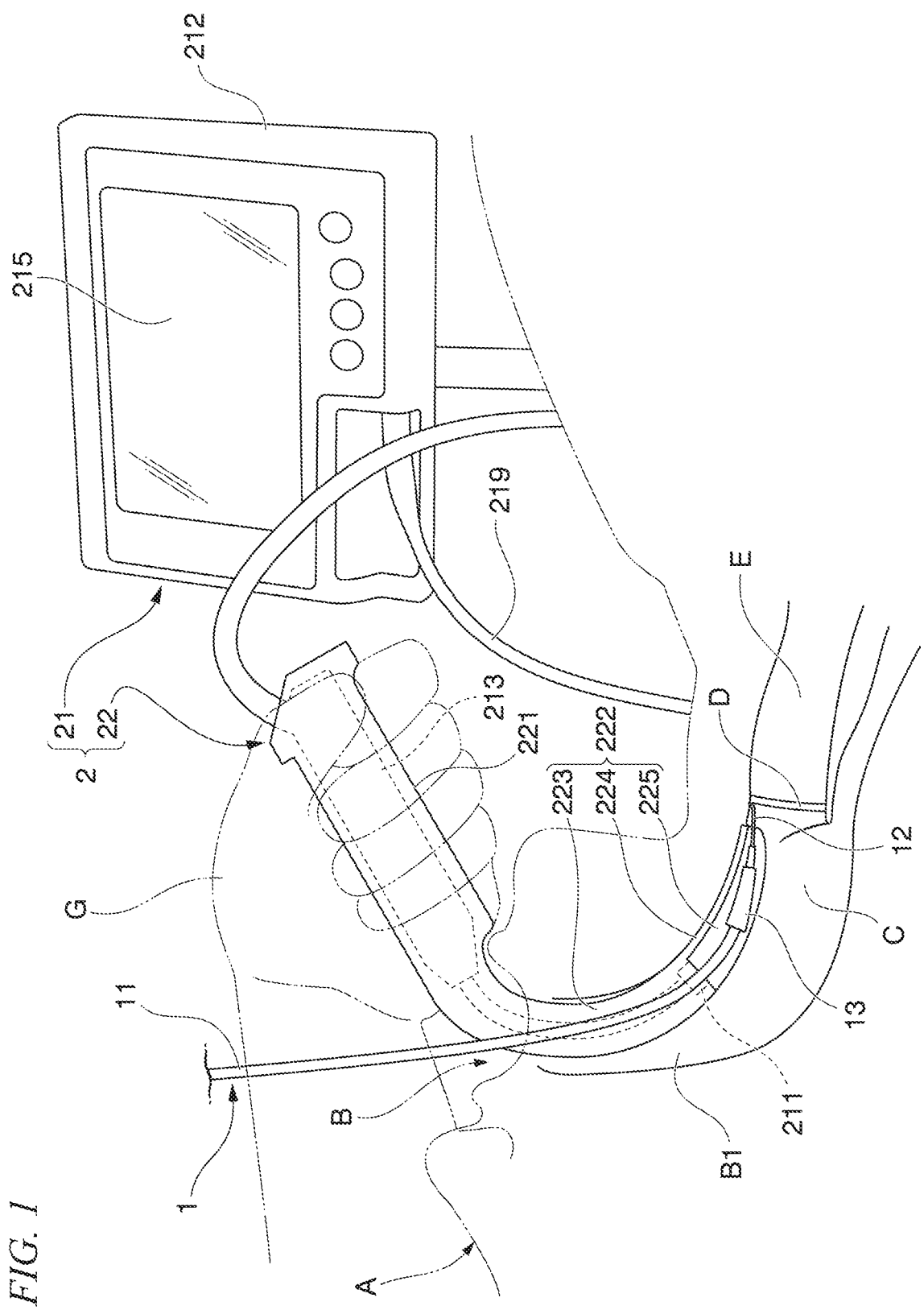
FIG. 1 is a view showing a state in which a tracheal tube insertion aid kit according to one embodiment of the present invention is used.

FIG. 1 is a view showing a state in which the tracheal tube insertion aid kit 1 is used. In the present embodiment, an example in which the tracheal tube insertion aid kit 1 is used when performing anesthesia on a patient A will be described. The tracheal tube insertion aid kit 1 assists in inserting a tracheal tube 9 (see FIG. 7) from an oral cavity B of the patient A into an endotracheal space E through a glottis D. The tracheal tube 9 is a circular tube member having flexibility that is inserted into the endotracheal space E.

The tracheal tube insertion aid kit 1 is used while a larynx C is observed and the glottis D of the patient A is indirectly viewed using an indirect glottis viewing type laryngoscope 2. In the following description, the indirect glottis viewing type laryngoscope 2 is simply referred to as the laryngoscope 2.

The laryngoscope 2 includes a laryngoscope main body 21 and a blade 22. The blade 22 is a member inserted into an intraoral space B1 of the patient A. The blade 22 is formed in a J-shaped container shape using, for example, a transparent resin material. A base end of the blade 22 is open.

The blade 22 includes a grip part 221 and an insertion part 222.

The grip part 221 is formed in an I-shaped cylindrical shape. The grip part 221 is a portion gripped by a hand G of a user of the laryngoscope 2, for example, a doctor.

The insertion part 222 is formed in a U shape. The insertion part 222 is a portion inserted into the intraoral space B1 of the patient A. The insertion part 222 includes an insertion part main body 223, a protruding part 224, and an attachment part 225. The insertion part main body 223 is formed at a distal end of the grip part 221. The insertion part main body 223 is formed in a curved shape. The insertion part main body 223 is formed in a container shape whose distal end is closed.

The protruding part 224 is formed on one side of the distal end of the insertion part main body 223. The protruding part 224 is formed in a curved shape and a plate shape. A distal end of the protruding part 224 is disposed toward the glottis D. The protruding part 224 is a portion that presses an epiglottis (not shown).

The attachment part 225 is formed to be coupled to the distal end of the insertion part main body 223 and the protruding part 224. The attachment part 225 is formed in a blade shape. The attachment part 225 is a portion to which a holding part 13 of the tracheal tube insertion aid kit 1 to be described below is attached.

The laryngoscope main body 21 includes an illumination unit (not shown), a camera 211, a display device 212, and a grip part 213. The illumination unit is disposed at a distal end portion inside the insertion part main body 223 and illuminates the larynx C. The camera 211 is disposed at the distal end portion inside the insertion part main body 223 and images the larynx C.

The display device 212 includes a monitor 215. The display device 212 is connected to the camera 211 and the illumination unit with a cable 219. The cable 219 has a portion on one side disposed inside the blade 22 and a portion on the other side pulled out from the base end of the blade 22. A control unit (not shown) is included inside the display device 212. The control unit controls operations of the camera 211 and the illumination unit. When the illumination unit and the camera 211 are turned on, the illumination unit illuminates the larynx C and the camera 211 images the larynx C. The display device 212 displays an image of the larynx C captured by the camera 211 on the monitor 215.

The grip part 213 is disposed inside the grip part 221 of the blade 22. The grip part 213 is connected to a portion on one side of the cable 219. The grip part 213 is a portion gripped by the hand G of a user of the laryngoscope 2, for example, a doctor, via the grip part 221 of the blade 22.

Next, a configuration of the tracheal tube insertion aid kit 1 will be described. The tracheal tube insertion aid kit 1 is attached to the attachment part 225 of the blade 22.

Figure 2:
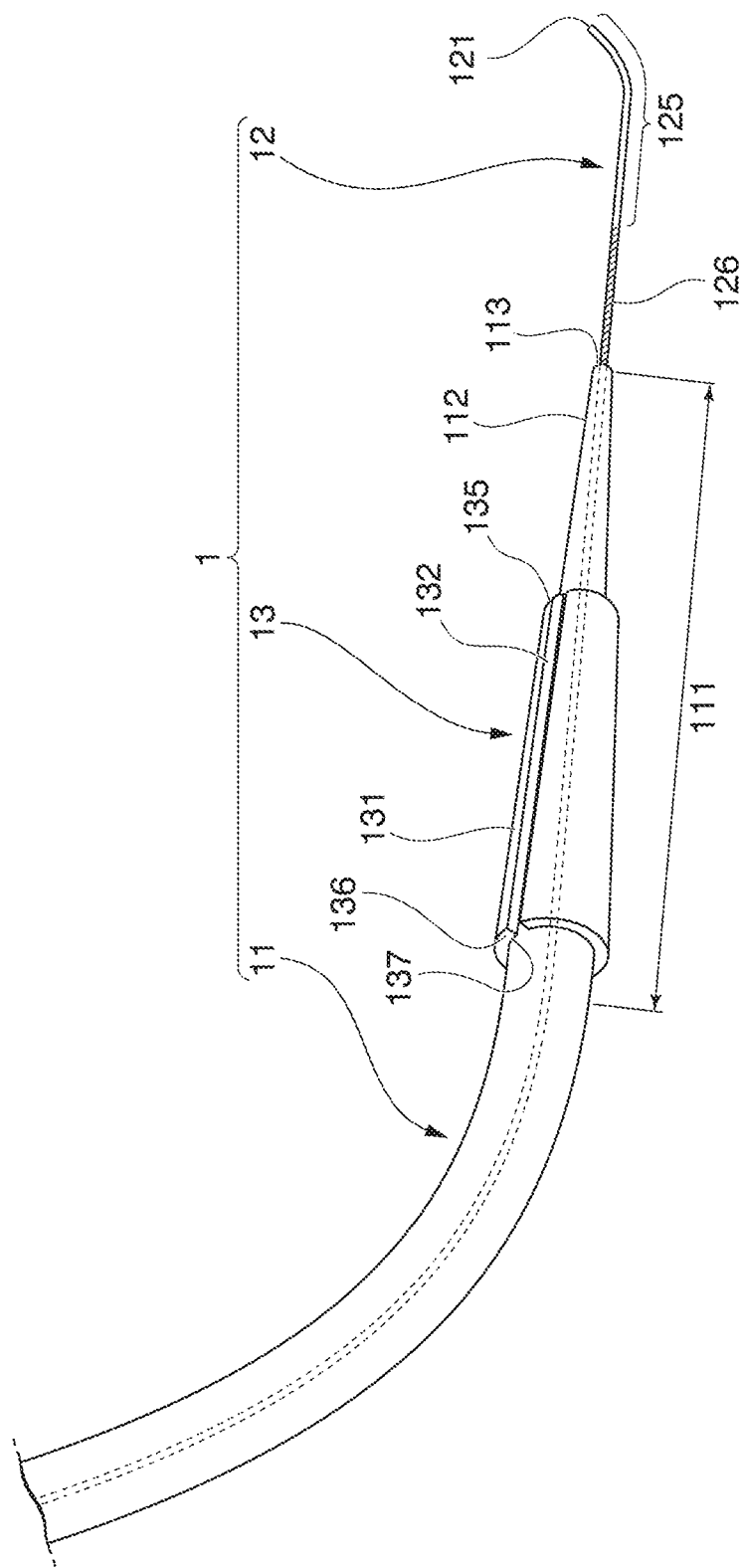
FIG. 2 is a perspective view of the tracheal tube insertion aid kit of the embodiment.

FIG. 2 is a perspective view of the tracheal tube insertion aid kit 1.

The tracheal tube insertion aid kit 1 includes a guide tube 11, a guide wire 12, and the holding part 13.

Figure 3:
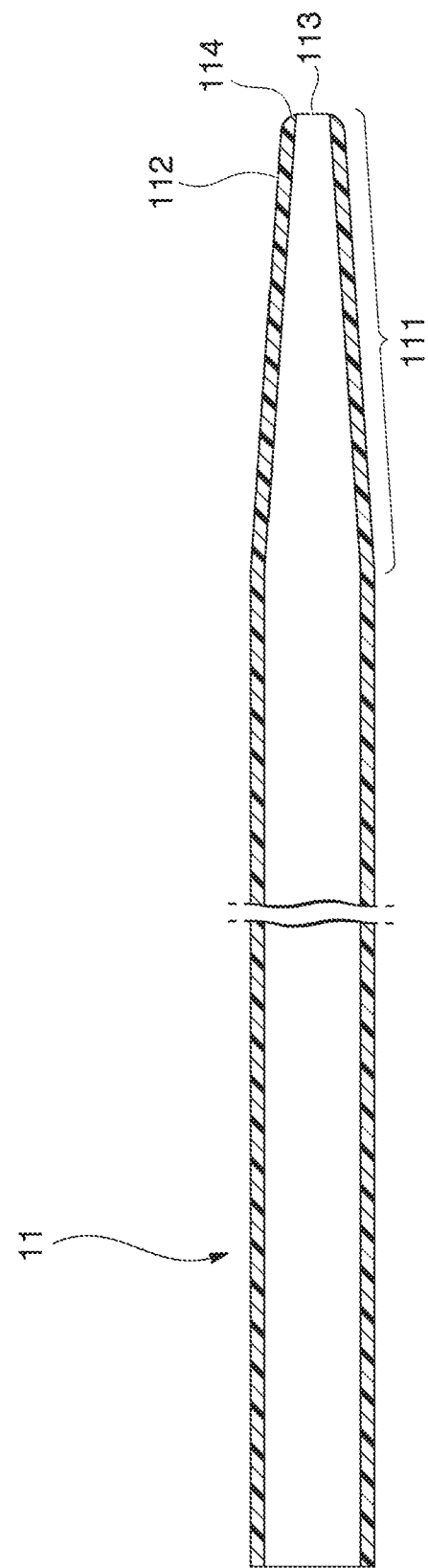
FIG. 3 is a cross-sectional view of a guide tube of the embodiment.

FIG. 3 is a cross-sectional view of the guide tube 11.

The guide tube 11 is, for example, a gum elastic bougie and is formed in a circular tube shape having flexibility. As shown in FIG. 1, the guide tube 11 is formed to be insertable into the endotracheal space E from the oral cavity B of the patient A through the glottis D. As shown in FIG. 3, a portion 111 on a distal end side of the guide tube 11 is formed in a tapered shape that becomes gradually thinner. A corner 114 of a distal end 113 of the guide tube 11 is formed to be rounded. The distal end 113 of the guide tube 11 is an end of a side to be inserted into the intraoral space B1. The portion 111 on the distal end side of the guide tube 11 is disposed at the larynx C before the guide tube 11 is inserted into the endotracheal space E and is disposed in the endotracheal space E when the guide tube 11 is inserted into the endotracheal space E.

A material of the guide tube 11 may be one that allows the guide tube 11 not to get caught when inserted into the endotracheal space E from the oral cavity B of the patient A through the glottis D and allows the tracheal tube 9 to slide when the tracheal tube 9 moves along the guide tube 11. In other words, the material of the guide tube 11 may be one having a smooth surface. As the material of the guide tube 11, a fluorine resin is an exemplary example. The guide tube 11 of the present embodiment may be formed by cutting one used as a catheter for endotracheal tube replacement (a tube exchanger) to an appropriate length.

As shown in FIG. 2, the guide wire 12 is formed such that it can be inserted through the inside of the guide tube 11. The guide wire 12 is formed such that it can be inserted into the endotracheal space E from the oral cavity B of the patient A through the glottis D. As the guide wire 12, a guide wire for endoscopic retrograde cholangiopancreatography (ERCP) is used. ERCP is an examination for imaging the bile duct or the pancreatic duct using an endoscope. The guide wire 12 may be formed of, for example, a metal material. The guide wire 12 is formed to be able to move straight. A distal end part 121 of the guide wire 12 is bent. The distal end part 121 of the guide wire 12 is coated with, for example, a urethane resin. Thereby, a surface of the distal end part 121 is soft. A portion 125 on a distal end side of the guide wire 12 is a portion disposed in the endotracheal space E. A visual marker 126 that is visible through the monitor 215 of the laryngoscope 2 is provided in a spiral shape on the base side of the guide wire 12 with respect to the portion 125 on the distal end side thereof. Thereby, a doctor who is the user of the laryngoscope 2 can ascertain the degree of insertion of the guide wire 12 into the endotracheal space E.

As shown in FIG. 1, the holding part 13 is provided at a portion of the blade 22 that can be observed on the monitor 215 of the laryngoscope 2. Specifically, the holding part 13 is provided in the attachment part 225 on a distal end side with respect to the camera 211 in the blade 22. The holding part 13 is integrally formed on the attachment part 225.

As shown in FIG. 2, the holding part 13 detachably holds the guide tube 11 in a state in which the distal end 113 of the guide tube 11 is disposed on a distal end side of the blade 22. Specifically, the holding part 13 is formed in a circular tube shape.

A first end 135 of the holding part 13 is provided on the distal end side of the blade 22. The holding part 13 is formed in a tapered shape from a second end 136 side (left side in FIG. 2) toward the first end 135. The holding part 13 detachably holds the portion 111 on the distal end side of the guide tube 11 in a state in which the portion 111 is inserted from the second end 136 side through an inside 137 of the holding part 13. A distal end part 112 of the guide tube 11 protrudes from the first end 135 side of the holding part 13.

A slit 132 which allows the guide wire 12 to be exposed to the outside while inserted through the inside 137 of the holding part 13 is provided in an axial direction of a circumferential surface 131 of the holding part 13.

Next, a method of inserting the tracheal tube 9 using the tracheal tube insertion aid kit 1 will be described.

First, the portion 111 on the distal end side of the guide tube 11 is inserted into the holding part 13 provided on the attachment part 225 of the blade 22 of the laryngoscope 2 and then held.

Next, the portion on the distal end side of the guide tube 11 is bent while being adjusted, and in this state, the blade 22 is inserted into the intraoral space B1 of the patient A.

Next, an epiglottis is pressed by the protruding part 224 of the blade 22 and the guide tube 11 is disposed.

Next, the camera 211 and the illumination unit are turned on to image the larynx C, and an image of the larynx C is displayed on the monitor 215.

When the distal end 113 of the guide tube 11 is not directed toward the glottis D, the blade 22 is removed from the intraoral space B1, and a bending angle of the distal end part 112 is adjusted again so that the distal end of the guide tube 11 is directed toward the glottis D.

After the bending angle is adjusted, the blade 22 is inserted into the intraoral space B1 and the guide tube 11 is arranged. When the distal end 113 of the guide tube 11 is directed toward the glottis D, the process proceeds to the next operation, and when the distal end 113 of the guide tube 11 is not directed toward the glottis D, the bending angle of the distal end part 112 is adjusted until the distal end 113 of the guide tube 11 is directed toward the glottis D.

Next, the guide wire 12 is inserted into the guide tube 11 from a base end of the guide tube 11 and is taken out on the distal end side of the guide tube 11.

Next, as shown in FIG. 4, the guide wire 12 is made to move straight and pass through the glottis D, and is inserted into the endotracheal space E.

Next, when a distal end of the visual marker 126 of the guide wire 12 reaches the glottis D, the guide wire 12 stops moving straight. Thereby, the portion 125 on the distal end side of the guide wire 12 is disposed in the endotracheal space E.

Next, as shown in FIG. 5, the guide tube 11 is pulled out to be removed from the holding part 13 and exposed to the outside of the holding part 13.

Next, by operating the guide tube 11, the guide wire 12 is moved outward in a radial direction of the holding part 13 to pass through the slit 132 of the holding part 13 and is exposed to the outside of the holding part 13. As a result, a path for guiding the guide tube 11 in which the guide tube 11 passes through the glottis D and is inserted into the endotracheal space E is formed by the guide wire 12.

Next, as shown in FIG. 6, the guide tube 11 is made to move straight by being guided along the guide wire 12 and inserted into the endotracheal space E through the glottis D, and thereby the portion 111 on the distal end side is arranged.

Next, the guide wire 12 is pulled out of the guide tube 11. As a result, a path for guiding the tracheal tube 9 so that the tracheal tube 9 passes through the glottis D from the oral cavity B and is inserted into the endotracheal space E is formed by the guide tube 11.

Next, as shown in FIG. 7, the tracheal tube 9 is made to move straight by being guided along the guide tube 11 and inserted into the endotracheal space E through the glottis D, and thereby the distal end side is disposed.

Finally, the guide tube 11 is pulled out of the endotracheal space E and taken out to the outside of the oral cavity B.

As described above, insertion of the tracheal tube 9 using the tracheal tube insertion aid kit 1 ends.

Next, the operation and effects of the tracheal tube insertion aid kit 1 of the present embodiment will be described.

The tracheal tube insertion aid kit 1 of the present embodiment assists in inserting the tracheal tube 9 from the oral cavity B of the patient A into the endotracheal space E through the glottis D using the indirect glottis viewing type laryngoscope 2.

The tracheal tube insertion aid kit 1 of the present embodiment includes the guide tube 11 formed such that it can be inserted into the endotracheal space E from the oral cavity B through the glottis D, and the guide wire 12 formed such that it can be inserted through the guide tube 11 and can be inserted into the endotracheal space E from the oral cavity B through the glottis D, in which at least the portion 111 on the distal end side of the guide tube 11 has flexibility.

According to this configuration, after the guide wire 12 is inserted and arranged in the endotracheal space E, by inserting and disposing the guide tube 11 guided by the guide wire 12 in the endotracheal space E, the tracheal tube insertion aid kit 1 of the present embodiment can insert the tracheal tube 9 along the guide tube 11 into the endotracheal space E. Since at least the portion 111 on the distal end side of the guide tube 11 has flexibility, a bent state of the portion 111 on the distal end side of the guide tube 11 can be adjusted according to a difference in position of the glottis D or the like for each patient A. Therefore, the tracheal tube insertion aid kit 1 of the present embodiment can easily insert the tracheal tube 9 into the endotracheal space E.

Also, the tracheal tube insertion aid kit 1 of the present embodiment is used together with the laryngoscope 2. Accordingly, when the laryngoscope 2 is used to observe the larynx C of the patient A or treat the larynx C, the tracheal tube insertion aid kit 1 may not be used. Therefore, the tracheal tube insertion aid kit 1 of the present embodiment can impart wide applicability to the laryngoscope 2 compared to a laryngoscope in which a tracheal tube is equipped.

In the tracheal tube insertion aid kit 1 of the present embodiment, the portion 111 on the distal end side of the guide tube 11 is formed in a tapered shape. Thereby, the guide tube 11 can easily pass through the glottis D. Therefore, the tracheal tube insertion aid kit 1 according to the present embodiment can improve workability of the operation involved in insertion of the tracheal tube 9.

In the tracheal tube insertion aid kit 1 of the present embodiment, the guide tube 11 is formed such that the corner 114 at the portion 111 on the distal end side is formed to be rounded. Thereby, when the guide tube 11 is inserted into the endotracheal space E, damage can be limited even when the distal end of the guide tube 11 hits a portion from the intraoral space B1 to the endotracheal space E. Therefore, the tracheal tube insertion aid kit 1 according to the present embodiment can prevent damage to a portion from the intraoral space B1 to the endotracheal space E in the operation for inserting the tracheal tube 9.

In the tracheal tube insertion aid kit 1 according to the present embodiment, the holding part 13 detachably holding the guide tube 11 in a state in which the distal end 113 of the guide tube 11 is disposed on the distal end side of the blade 22 is provided in the blade 22 of the laryngoscope 2 at a portion that is observable with the laryngoscope 2 (the attachment part 225 in the present embodiment). As a result, when the blade 22 is inserted into the intraoral space B1 in a state in which the guide tube 11 is held by the holding part 13, the guide tube 11 is disposed with the distal end 113 directed to the glottis D.

Therefore, the guide tube 11 can be easily arranged compared to a case in which the guide tube 11 is inserted alone into the intraoral space B1, and thus damage to the intraoral space B1 due to the distal end 113 of the guide tube 11 can be limited. Therefore, the tracheal tube insertion aid kit 1 of the present embodiment can prevent damage in the intraoral space B1 while improving the workability at the time of inserting the tracheal tube 9.

In the tracheal tube insertion aid kit 1 of the present embodiment, the holding part 13 is formed in a tubular shape and is formed in a tapered shape toward the distal end side of the blade 22 and detachably holds the guide tube 11 with the guide tube 11 inserted through the inside 137. A slit 132 which allows the guide wire 12 to be exposed to the outside while inserted through the inside 137 of the holding part 13 is provided on the circumferential surface 131 of the holding part 13. Thereby, the guide tube 11 can be easily removed from the holding part 13 by pulling the guide tube 11. The guide wire 12 can be easily removed from the holding part 13 by operating the guide tube 11 to move the guide wire outward in a radial direction of the holding part 13 and pass through the slit 132. Therefore, the tracheal tube insertion aid kit 1 of the present embodiment can further improve the workability at the time of inserting the tracheal tube 9.

In the tracheal tube insertion aid kit 1 of the present embodiment, since the holding part 13 is integrally formed on the blade 22, the number of parts can be reduced compared to a case in which the holding part 13 and the blade 22 are separately formed. Therefore, it is possible to achieve cost reduction in the tracheal tube insertion aid kit 1 of the present embodiment.

In the tracheal tube insertion aid kit 1 of the present embodiment, a conventional guide wire (guide wire for ERCP) is used for the guide wire 12. Thus, it is not necessary to newly manufacture the guide wire 12. Therefore, it is possible to achieve a further cost reduction in the tracheal tube insertion aid kit 1 of the present embodiment.

In the tracheal tube insertion aid kit 1 of the present embodiment, a catheter for endotracheal tube replacement may be cut at the site to be used as the guide tube 11. Without cutting, it can be used as a catheter for endotracheal tube replacement. Therefore, it is not necessary to newly manufacture the guide tube 11. Therefore, it is possible to achieve a further cost reduction in the tracheal tube insertion aid kit 1 of the present embodiment.

In the tracheal tube insertion aid kit 1 of the present embodiment, the holding part 13 formed in a tapered shape causes the portion 111 on the distal end side of the guide tube 11 formed in a tapered shape to be inserted therethrough and held. Therefore, since the guide tube 11 is attachable and detachable by being inserted into and removed from the second end 136 of the holding part 13, the operation of attaching and detaching the guide tube 11 can be easily performed with a simple configuration.

Another Embodiment

Next, another embodiment of the present invention will be described. Detailed description of the same configuration as those of the above embodiment will be omitted.

Figure 8:
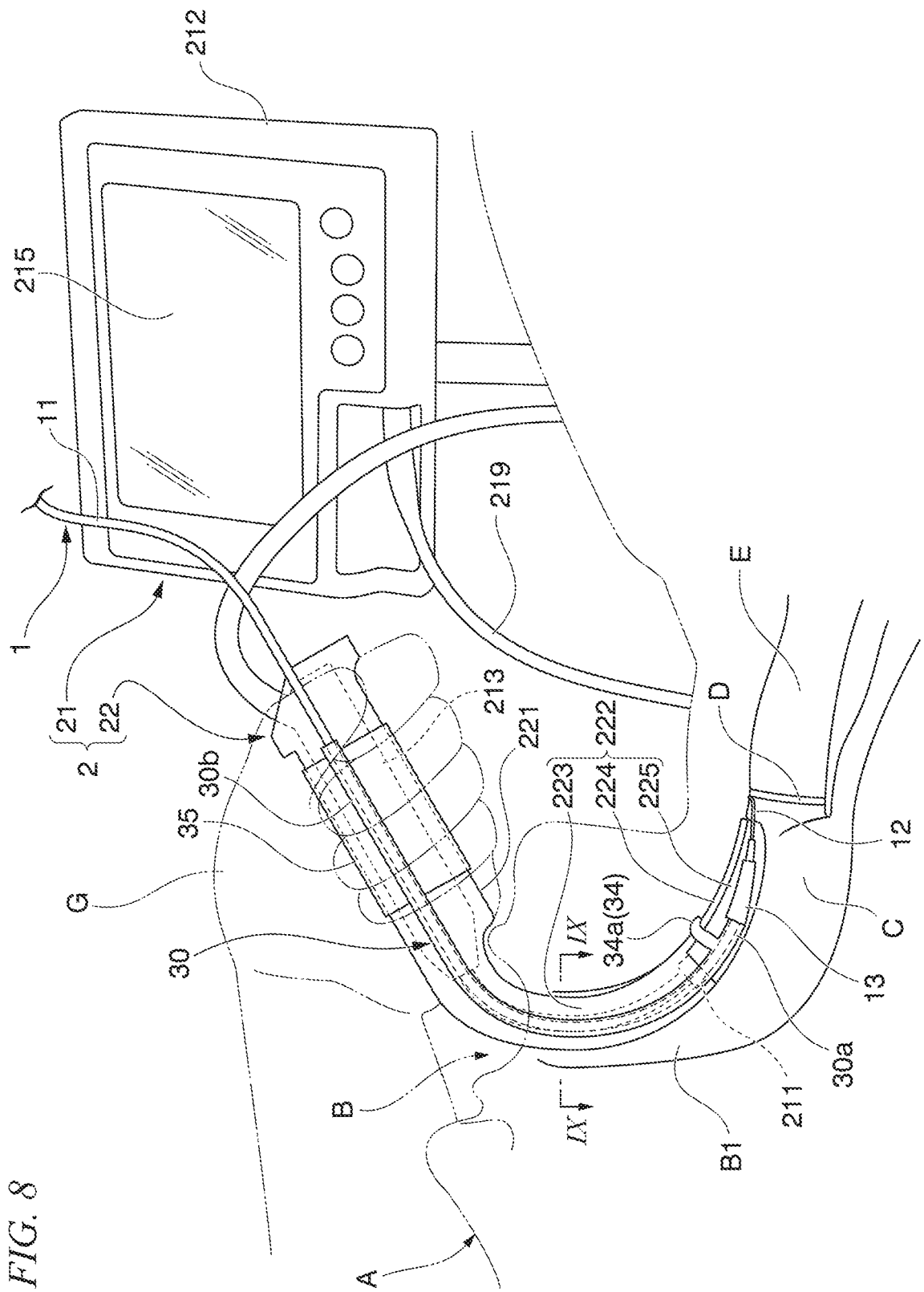
FIG. 8 is a view showing a state in which a tracheal tube insertion aid kit according to another embodiment is used.

FIG. 8 is a view showing a state in which a tracheal tube insertion aid kit according to another embodiment is used.

Figure 9:
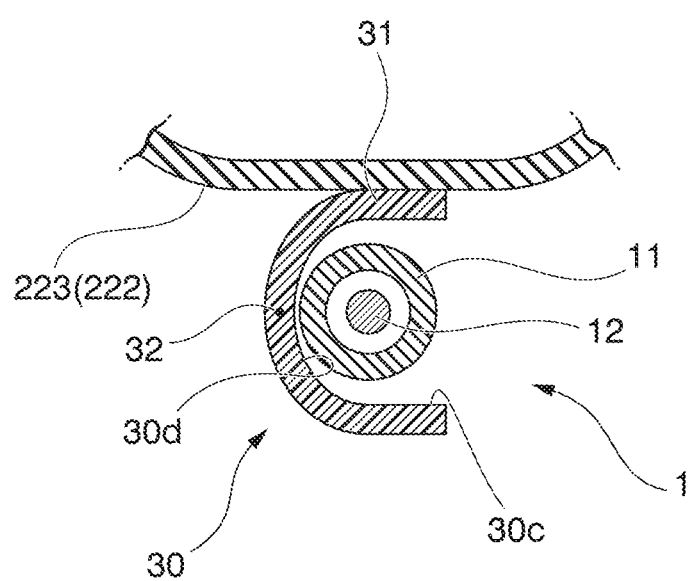
FIG. 9 is a cross-sectional view perpendicular to a direction in which an introducing member extends, taken along line IX-IX in FIG. 8.

FIG. 9 is a cross-sectional view perpendicular to a direction in which an introducing member extends, taken along line IX-IX in FIG. 8.

As shown in FIG. 8, a tracheal tube insertion aid kit 1 according to another embodiment includes an introducing member 30 for introducing a guide tube 11 into an endotracheal space E.

The introducing member 30 is disposed to extend along a blade 22 on a side of the blade 22 of a laryngoscope 2 formed in an arc shape. The introducing member 30 introduces the guide tube 11 into the endotracheal space E.

The introducing member 30 is a so-called free rod, and as shown in FIG. 9, may include, for example, an exterior part 31 formed of an easily deformable resin material, and a core 32 formed of a metal material such as a wire which can be easily deformed and can be held in a predetermined shape. Thereby, the introducing member 30 is deformable and can be held in a predetermined shape.

As shown in FIG. 8, a holding part 13 is provided at first end portion 30a of end portions of the introducing member 30 which is disposed on one distal end side of the blade 22. An engaging part 34 engageable with the blade 22 is provided at first end portion 30a of the introducing member 30. The engaging part 34 includes, for example, a claw part 34a that can be engaged with an edge portion of the blade 22 or the like.

At the second end portion 30b of the introducing member 30, a grab part 35 joined to the introducing member 30 is provided. The grab part 35 is formed in a deformable plate shape. The grab part 35 is disposed to be wound around a grip part 221 of the blade 22 and is gripped by the hand G of a user together with the grip part 221 of the blade 22.

The introducing member 30 is positioned when the first end portion 30a is engaged and fixed to the blade 22 by the engaging part 34 and the grab part 35 of the second end portion 30b is gripped by the hand G of the user together with the grip part 221.

Here, as shown in FIG. 9, a cross-sectional shape perpendicular to a direction in which the introducing member 30 extends is formed in a U shape having an opening 30c. The opening 30c of the introducing member 30 opens on an inner side in a radial direction of an insertion part 222 of the blade 22 formed in an arc shape. The guide tube 11 is introduced along the introducing member 30 while it is in contact with an inner wall 30d of the introducing member 30.

Next, the operation and effects of the tracheal tube insertion aid kit 1 according to another embodiment will be described.

The tracheal tube insertion aid kit 1 according to another embodiment includes the introducing member 30 which is deformable and can be held in a predetermined shape, and the holding part 13 is configured to be provided at the first end portion 30a of the end portions of the introducing member 30 which is disposed on one distal end side of the blade 22. Thereby, the guide tube 11 can be introduced after the introducing member 30 is deformed according to a difference in position of the glottis D or the like for each patient A and the position of the holding part 13 is adjusted. Since the holding part 13 is provided at the first end portion 30a of the end portions of the introducing member 30 which is disposed on the distal end side of the blade, the guide tube 11 can be easily held by the holding part 13 after being introduced. Therefore, the tracheal tube insertion aid kit 1 of another embodiment can further improve the workability at the time of inserting the tracheal tube 9.

In the tracheal tube insertion aid kit 1 according to another embodiment, the grab part 35 gripped by the hand G of the user together with the grip part 221 of the blade 22 is configured to be provided at the second end portion 30b of the introducing member 30. Thereby, the user can insert the guide wire 12 into the endotracheal space E in a state in which the introducing member 30 and the guide tube 11 are reliably positioned. Therefore, the tracheal tube insertion aid kit 1 according to another embodiment can further improve the workability at the time of inserting the tracheal tube 9.

In the tracheal tube insertion aid kit 1 according to another embodiment, a cross-sectional shape perpendicular to the direction in which the introducing member 30 extends is formed in a U shape having an opening 30c on an inner side in the radial direction of the insertion part 222 of the blade 22 formed in an arc shape. Thus, the user can introduce the guide tube 11 from the U-shaped opening side and introduce the guide tube while it is in contact with the inner wall 30d of the introducing member 30. Therefore, the tracheal tube insertion aid kit 1 according to another embodiment can further improve the workability at the time of inserting the tracheal tube 9.

In the tracheal tube insertion aid kit 1 according to another embodiment, since the engaging part 34 engageable with the blade 22 is provided at the first end portion 30a of the introducing member 30, the holding part 13 can be reliably positioned by fixing the first end portion 30a of the introducing member 30 to the blade 22 by the engaging part 34. Therefore, the tracheal tube insertion aid kit 1 according to another embodiment can further improve the workability at the time of inserting the tracheal tube 9.

As described above, although the embodiments of the present invention have been described in detail with reference to the drawings, the specific configuration is not limited to the embodiments, and change in design to such an extent that it does not deviate from the gist of the present invention is included in the present invention.

In the embodiment, the holding part 13 is integrally formed on the attachment part 225 of the blade 22 but may be detachably attached to the attachment part 225.

In the embodiment, the attachment part 225 is formed in the blade 22 to provide the holding part 13 in the blade 22, but the attachment part 225 is not necessarily required, and alternatively, for example, the holding part 13 may be integrally formed on the protruding part 224 or may be detachably attached thereto.

Although an example in which the tracheal tube insertion aid kit 1 is used when performing anesthesia on the patient A has been shown in the embodiment, the tracheal tube insertion aid kit 1 may also be used when using a tracheal tube to deliver oxygen into an endotracheal space of a patient at the time of rescue.

In the embodiment, a laryngoscope of indirect glottis viewing type using a camera is used as the indirect glottis viewing type laryngoscope, but a laryngoscope of indirect glottis viewing type using an optical element such as a lens or a prism may also be used.

In another embodiment, a cross-sectional shape perpendicular to the direction in which the introducing member 30 extends is formed in a U shape having the opening 30c on the inner side in the radial direction of the insertion part 222, but the present invention is not limited thereto, and it may be formed in a flat plate shape or V shape.

The introducing member 30 is a so-called free rod and includes the exterior part 31 formed of a resin material and the core 32 formed of a metal material such as a wire, but the present invention is not limited to the configuration. Thus, for example, the introducing member 30 may be entirely formed only of a resin material or may be formed only of a metal material.

In another embodiment, the engaging part 34 engageable with the blade 22 is provided at first end portion 30a of the introducing member 30, but the engaging part 34 may not be provided. An aspect of the engaging part 34 is not limited to the claw part 34a that can be engaged with an edge portion of the blade 22 or the like, and may be, for example, a surface fastener or the like.

In another embodiment, the grab part 35 gripped by the user is provided at the second end portion 30b of the introducing member 30, but the grab part 35 may not be provided.

In addition, the components in the above-described embodiments can be appropriately replaced with well-known components without departing from the spirit and scope of the present invention.

REFERENCE SIGNS LIST

1 Tracheal tube insertion aid kit
2 Laryngoscope
9 Tracheal tube
11 Guide tube
12 Guide wire
13 Holding part
30 Introducing member
30a First end portion
30b Second end portion
30c Opening
34 Engaging part
35 Grab part
113 Distal end of guide tube
114 Angle of distal end of guide tube
131 Circumferential surface of holding part
132 Slit
137 Inside of holding part
222 Insertion part
A Patient
B Oral cavity
D Glottis
E Endotracheal space

The invention claimed is:

1. A tracheal tube insertion aid kit having an indirect glottis viewing type laryngoscope and configured to assist in inserting a tracheal tube from an oral cavity of a patient into an endotracheal space through a glottis using the indirect glottis viewing type laryngoscope, the tracheal tube insertion aid kit comprising:
the indirect glottis viewing type laryngoscope;
a guide tube formed to be insertable into the endotracheal space from the oral cavity through the glottis;
a guide wire formed to be insertable through the inside of the guide tube and insertable into the endotracheal space from the oral cavity through the glottis,
wherein at least a portion on a distal end side of the guide tube has flexibility; and
a holding part detachably holding the guide tube in a state such that, when the kit is used to insert the tracheal tube into the endotracheal space of the patient, a distal end of the guide tube is disposed on a distal end side of a blade of the laryngoscope;
wherein the holding part is provided at a portion of the blade that is observable with the laryngoscope;

wherein the holding part is formed in a circular tube shape at a periphery of the guide tube and is formed in a tapered shape from a second end side toward a first end that is provided on the distal end side of the blade; and wherein a slit, which allows the guide wire to be exposed to the outside while inserted through the inside of the holding part and when the holding part is not coupled to the blade, is provided on a circumferential surface of the holding part, the slit lying fully within a plane that extends between the first end and the second end of the holding part and is tangent to the circumferential surface of the holding part.

2. The tracheal tube insertion aid kit according to claim 1, wherein the portion on the distal end side of the guide tube is formed in a tapered shape.

3. The tracheal tube insertion aid kit according to claim 1, wherein a corner of the portion on the distal end side of the guide tube is formed to be rounded.

4. The tracheal tube insertion aid kit according to claim 1, wherein the holding part is integrally formed on the blade.

5. The tracheal tube insertion aid kit according to claim 1, comprising:

an introducing member disposed to extend along the blade of the laryngoscope and configured to introduce the guide tube into the endotracheal space, wherein the introduction member is deformable and able to be held in a predetermined shape, and the holding part is provided at a first end portion of the introducing member which is disposed on the distal end side of the blade.

6. The tracheal tube insertion aid kit according to claim 5, wherein a grab part formed in a deformable plate shape and configured to be gripped by a user together with a grip part of the blade is provided at a second end portion of the introducing member.

7. The tracheal tube insertion aid kit according to claim 5, wherein the blade includes an insertion part formed to be curved in an arc shape and configured to be inserted into an intraoral space of the patient, wherein a cross-sectional shape perpendicular to a direction in which the introducing member extends is formed in a U shape having an opening on an inner side in a radial direction of the insertion part formed in an arc shape.

8. The tracheal tube insertion aid kit according to claim 5, wherein an engaging part engageable with the blade is provided at the first end portion of the introducing member.

* * * * *